United States Patent
Bandyopadhyay et al.

(10) Patent No.: US 11,263,450 B2
(45) Date of Patent: Mar. 1, 2022

(54) METHOD AND SYSTEM FOR PATTERN RECOGNITION IN A SIGNAL USING MORPHOLOGY AWARE SYMBOLIC REPRESENTATION

(71) Applicant: Tata Consultancy Services Limited, Mumbai (IN)

(72) Inventors: Soma Bandyopadhyay, Kolkata (IN); Arijit Ukil, Kolkata (IN); Chetanya Puri, Kolkata (IN); Rituraj Singh, Kolkata (IN); Arpan Pal, Kolkata (IN); C A Murthy, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 539 days.

(21) Appl. No.: 16/264,786

(22) Filed: Feb. 1, 2019

(65) Prior Publication Data
US 2019/0278971 A1    Sep. 12, 2019

(30) Foreign Application Priority Data
Mar. 7, 2018    (IN) .............................. 201821008463

(51) Int. Cl.
*G06K 9/00*    (2006.01)
*G06K 9/62*    (2006.01)
(Continued)

(52) U.S. Cl.
CPC ............ *G06K 9/0053* (2013.01); *A61B 5/349* (2021.01); *G06K 9/00536* (2013.01); *G06K 9/6222* (2013.01); *G06K 9/6223* (2013.01)

(58) Field of Classification Search
CPC .. A61B 5/349; G06K 9/0053; G06K 9/00536; G06K 9/6222; G06K 9/6223
See application file for complete search history.

(56) References Cited

U.S. PATENT DOCUMENTS

2009/0112106 A1*    4/2009    Zhang .................... A61B 5/349
                                                                    600/509
2010/0228136 A1*    9/2010    Keel ...................... A61B 5/318
                                                                    600/507
(Continued)

OTHER PUBLICATIONS

Syed, Z. et al. (Mar. 2007). "Clustering and Symbolic Analysis of Cardiovascular Signals: Discovery and Visualization of Medically Relevant Patterns in Long-Term Data Using Limited Prior Knowledge," *EURASIP Journal on Advances in Signal Processing*, vol. 2007; 17 pages.

(Continued)

*Primary Examiner* — Peet Dhillon
(74) *Attorney, Agent, or Firm* — Finnegan, Henderson, Farabow, Garrett & Dunner, LLP

(57) ABSTRACT

The present disclosure addresses the technical problem of information loss while representing a physiological signal in the form of symbols and for recognizing patterns inside the signal. Thus making it difficult to retain or extract any relevant information which can be used to detect anomalies in the signal. A system and method for anomaly detection and discovering pattern in a signal using morphology aware symbolic representation has been provided. The system discovers pattern atoms based on the strictly increasing and strictly decreasing characteristics of the time series physiological signal, and generate symbolic representation in terms of these pattern atoms. Additionally the method possess more generalization capability in terms of granularity. This detects discord/abnormal phenomena with consistency.

20 Claims, 4 Drawing Sheets

(51) Int. Cl.
    *A61B 5/0452*     (2006.01)
    *A61B 5/349*     (2021.01)

(56) References Cited

U.S. PATENT DOCUMENTS

| | | | |
|---|---|---|---|
| 2010/0239139 A1* | 9/2010 | Hunt | G06K 9/6218 |
| | | | 382/128 |
| 2012/0123279 A1* | 5/2012 | Brueser | A61B 5/1102 |
| | | | 600/481 |
| 2012/0215275 A1* | 8/2012 | Wenzel | A61B 5/02158 |
| | | | 607/19 |
| 2013/0046193 A1* | 2/2013 | Guttag | A61B 5/316 |
| | | | 600/509 |
| 2014/0073865 A1* | 3/2014 | Rodriguez-Llorente | |
| | | | G06K 9/0053 |
| | | | 600/301 |
| 2017/0340211 A1 | 11/2017 | Bandyopadhyay et al. | |

OTHER PUBLICATIONS

Lin, J. et al. "A Symbolic Representation of Time Series, with Implications for Streaming Algorithms," *DMKD '03 Proceedings of the 8th ACM SIGMOD Workshop on Research Issues in Data Mining and Knowledge Discovery*, Jun. 13, 2003, San Diego, CA; pp. 2-11.

Aghabozorgi, S. et al. (2015). "Time-series clustering—A decade review," *Information Systems*, vol. 53; pp. 16-38.

Fred, A. (2002). "Similarity Measures and Clustering of String Patterns," In *Pattern Recognition and String Matching*. D. Chen and X. Cheng ed., Kluwer Academic Publishers, pp. 1-39.

* cited by examiner

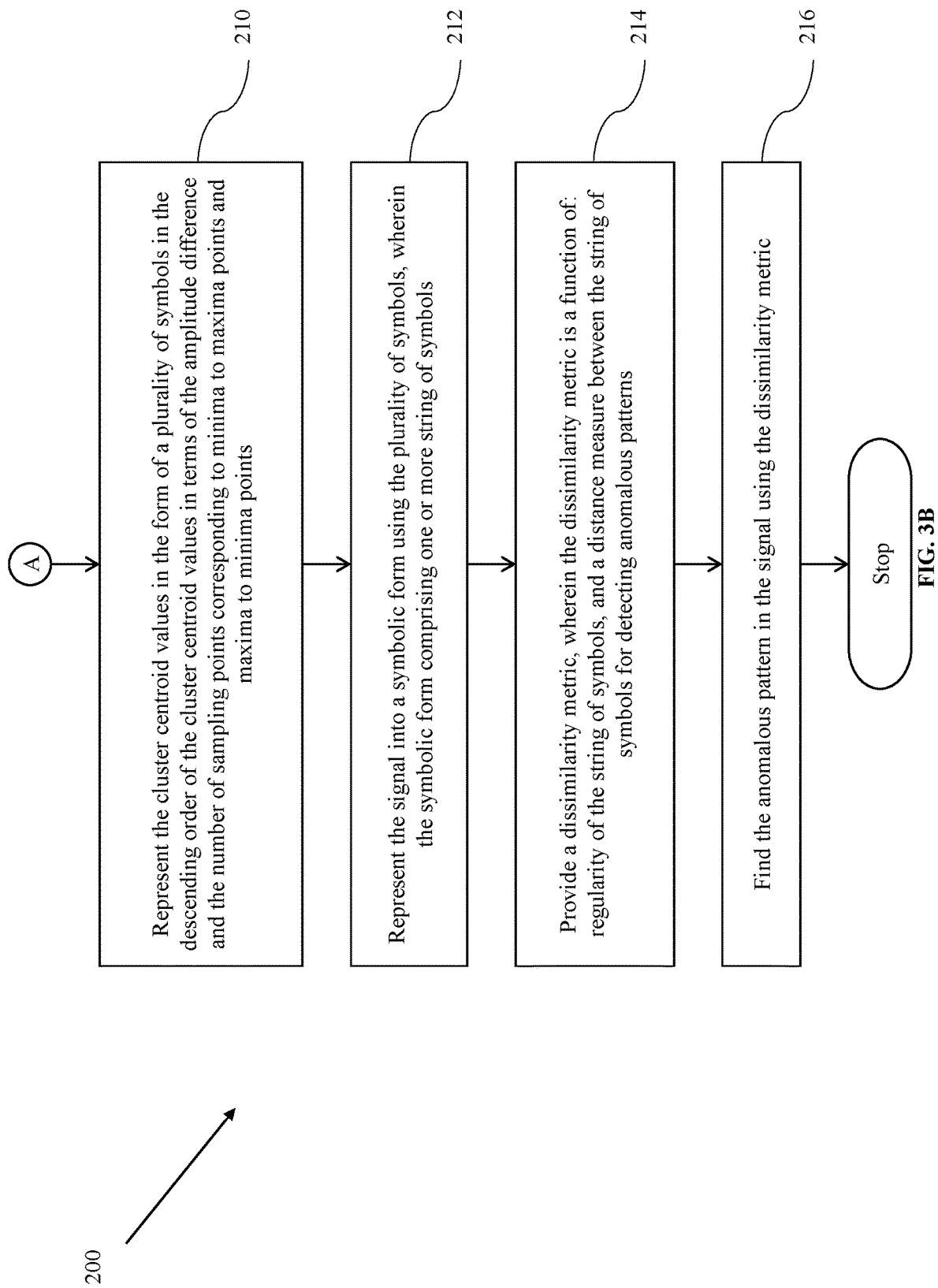

METHOD AND SYSTEM FOR PATTERN RECOGNITION IN A SIGNAL USING MORPHOLOGY AWARE SYMBOLIC REPRESENTATION

PRIORITY CLAIM

This U.S. patent application claims priority under 35 U.S.C. § 119 to: India Application No. 201821008463, filed on Mar. 7, 2018. The entire contents of the aforementioned application are incorporated herein by reference.

TECHNICAL FIELD

This disclosure relates generally to the field of physiological signal processing, and more particularly to a method and system for anomaly detection and discovering pattern in a physiological signal using morphology aware symbolic representation.

BACKGROUND

Signal processing of a physiological signal is a very well researched topic in the art. Various methods have been used to detect anomaly in the physiological signals, especially in the electrocardiogram (ECG) signal. Anomaly detection in a physiological signal refers to the problem of finding patterns that do not conform to an expected behavior of the monitored signal. These abnormal patterns could translate to significant information about the health of a person. There is a need to discriminate between the normal and anomalous phenomena inside the signals.

A few methods have also been used in the prior art to discover the abnormal pattern from the physiological signal using the symbolic representation of the signal. But there is general loss of information while discovering the pattern. One of the prior available method uses piecewise aggregate approximation (PAA) to convert time series signal into symbols. This method uses approximation techniques. There is a huge information loss of the signal during representation of signal in the form of symbol. The huge information loss can lead to improper anomaly detection.

Another prior art method uses user-defined parameters for the symbolic approximation. The parameters needs to be set and varies from signal to signal, which do not provide a generalized method for anomaly detection. Thus they do not provide reliable information for accurately classifying the healthy signal with the diseased signal.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for detecting anomaly and discovering pattern in a signal using symbolic representation of the signal, the system comprises as sensor, a memory and a processor. The sensor senses the signal from a person, wherein the signal is a time series signal with a plurality of time points. The processor further comprises a maxima minima finding module, a feature derivation module, a clustering module, a symbolic representation module for signal, a derivation module and anomaly detection module. The maxima and minima finding module finds a plurality of maxima points and a plurality of minima points in the signal, wherein the plurality of maxima points and the plurality of minima points are following morphology of the signal. The feature derivation module derives a plurality of features using the plurality of maxima points and the plurality of minima points which are adjacent to each other, wherein the plurality of features comprises an amplitude difference and a number of sampling points between minima to maxima points which are adjacent to each other and the amplitude difference and a number of sampling points between maxima to minima points which are adjacent to each other. The clustering module performs a proximity based clustering on the plurality of features to get a cluster centroid values corresponding to each of the plurality of features. The symbolic representation module for signal represents the cluster centroid values in the form of a plurality of symbols mapping of which is done in the descending order of the cluster centroid values in terms of the amplitude difference and the number of sampling points corresponding to minima to maxima points and maxima to minima points. This module further represents the signal into a symbolic form using the plurality of symbols, wherein the symbolic form comprising one or more string of symbols. The derivation module provides a dissimilarity metric, wherein the dissimilarity metric is a function of regularity of the string of symbols, and a distance measured between the strings of symbols for detecting anomalous patterns. The anomaly identification module detects the anomalous pattern in the signal using the dissimilarity metric.

In another aspect the embodiment here provides a method for detecting anomaly and discovering pattern in a signal using symbolic representation of the signal. Initially, the signal is sensed from a person using a sensor, wherein the signal is a time series signal with a plurality of time points. In the next step, a plurality of maxima points and a plurality of minima points are found in the signal, wherein the plurality of maxima points and the plurality of minima points are following morphology of the signal. In the next step a plurality of features are derived using the plurality of maxima points and the plurality of minima points which are adjacent to each other, wherein the plurality of features comprises amplitude difference and number of sampling points between minima to maxima points which are adjacent to each other and amplitude difference and number of sampling points between maxima to minima points which are adjacent to each other. In the next step, a proximity based clustering is performed on the plurality of features to get a cluster centroid values corresponding to each of the plurality of features. In the next step, the cluster centroid values are represented in the form of a plurality of symbols in the descending order of the cluster centroid values in terms of the amplitude difference as well as the number of sampling points corresponding to minima to maxima points and maxima to minima points. In the next step, the signal is represented into a symbolic form using the plurality of symbols, wherein the symbolic form comprising one or more string of symbols. In the next step, a dissimilarity metric is derived, wherein the dissimilarity metric is a function of regularity of the string of symbols and a distance measure between the strings of symbols for detecting anomalous patterns. And finally, the anomalous pattern is detected in the signal using the dissimilarity metric.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

In yet another aspect, a non-transitory computer readable medium is provided. The non-transitory computer-readable medium stores instructions which, when executed by a hardware processor, cause the hardware processor to perform actions comprising detecting anomaly and discovering pattern in a signal using symbolic representation of the signal. Initially, the signal is sensed from a person using a sensor, wherein the signal is a time series signal with a plurality of time points. In the next step, a plurality of maxima points and a plurality of minima points are found in the signal, wherein the plurality of maxima points and the plurality of minima points are following morphology of the signal. In the next step a plurality of features are derived using the plurality of maxima points and the plurality of minima points which are adjacent to each other, wherein the plurality of features comprises amplitude difference and number of sampling points between minima to maxima points which are adjacent to each other and amplitude difference and number of sampling points between maxima to minima points which are adjacent to each other. In the next step, a proximity based clustering is performed on the plurality of features to get a cluster centroid values corresponding to each of the plurality of features. In the next step, the cluster centroid values are represented in the form of a plurality of symbols in the descending order of the cluster centroid values in terms of the amplitude difference as well as the number of sampling points corresponding to minima to maxima points and maxima to minima points. In the next step, the signal is represented into a symbolic form using the plurality of symbols, wherein the symbolic form comprising one or more string of symbols. In the next step, a dissimilarity metric is derived, wherein the dissimilarity metric is a function of regularity of the string of symbols and a distance measure between the strings of symbols for detecting anomalous patterns. And finally, the anomalous pattern is detected in the signal using the dissimilarity metric.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which:

FIG. 3A-3B is a flowchart illustrating the steps involved in detecting anomaly and discovering pattern in the signal using symbolic representation of the signal according to an embodiment of the present disclosure.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
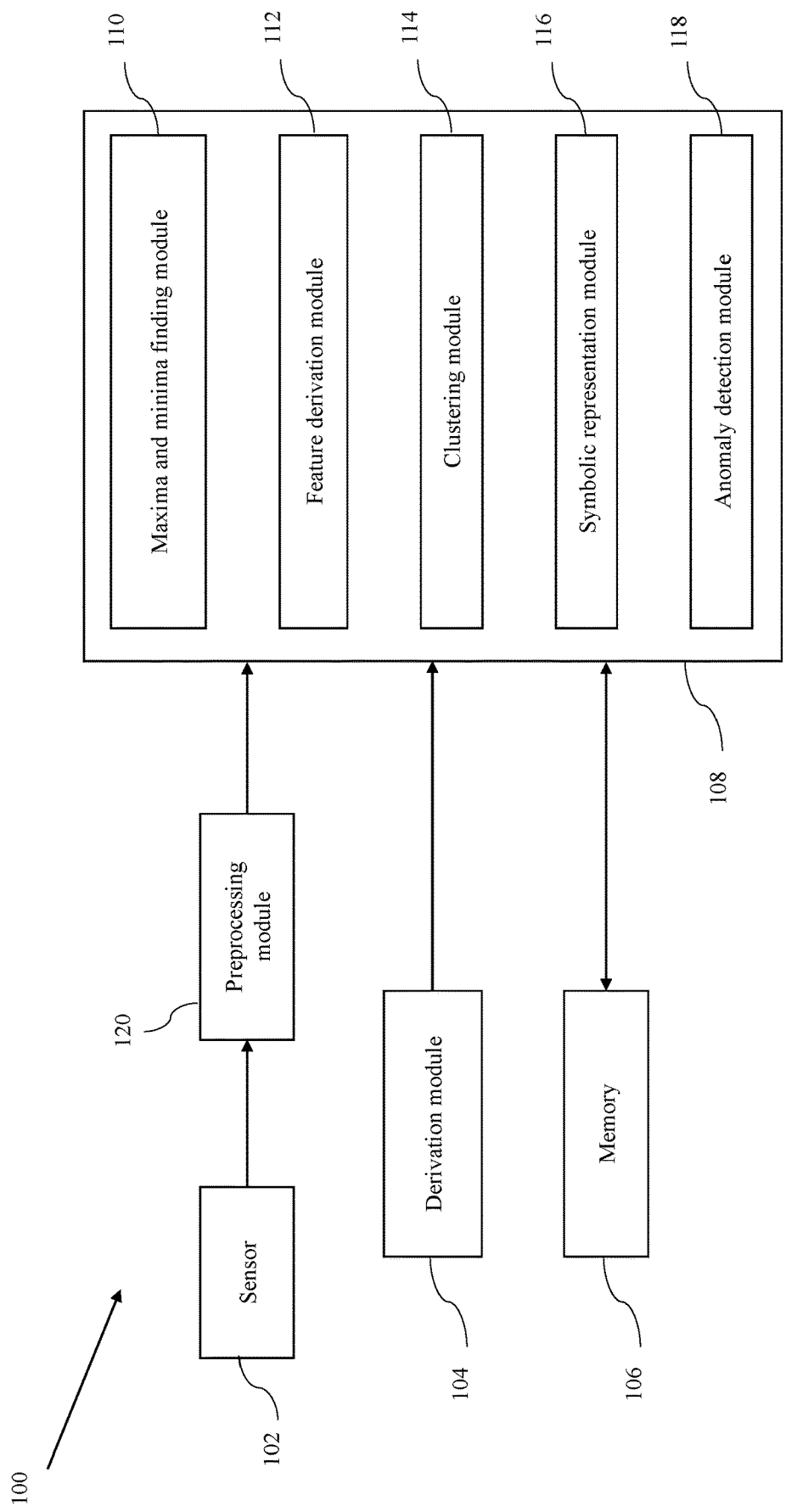
FIG. 1 illustrates a block diagram of a system for detecting anomaly and discovering pattern in a signal using symbolic representation of the signal according to an embodiment of the present disclosure.
Figure 2:
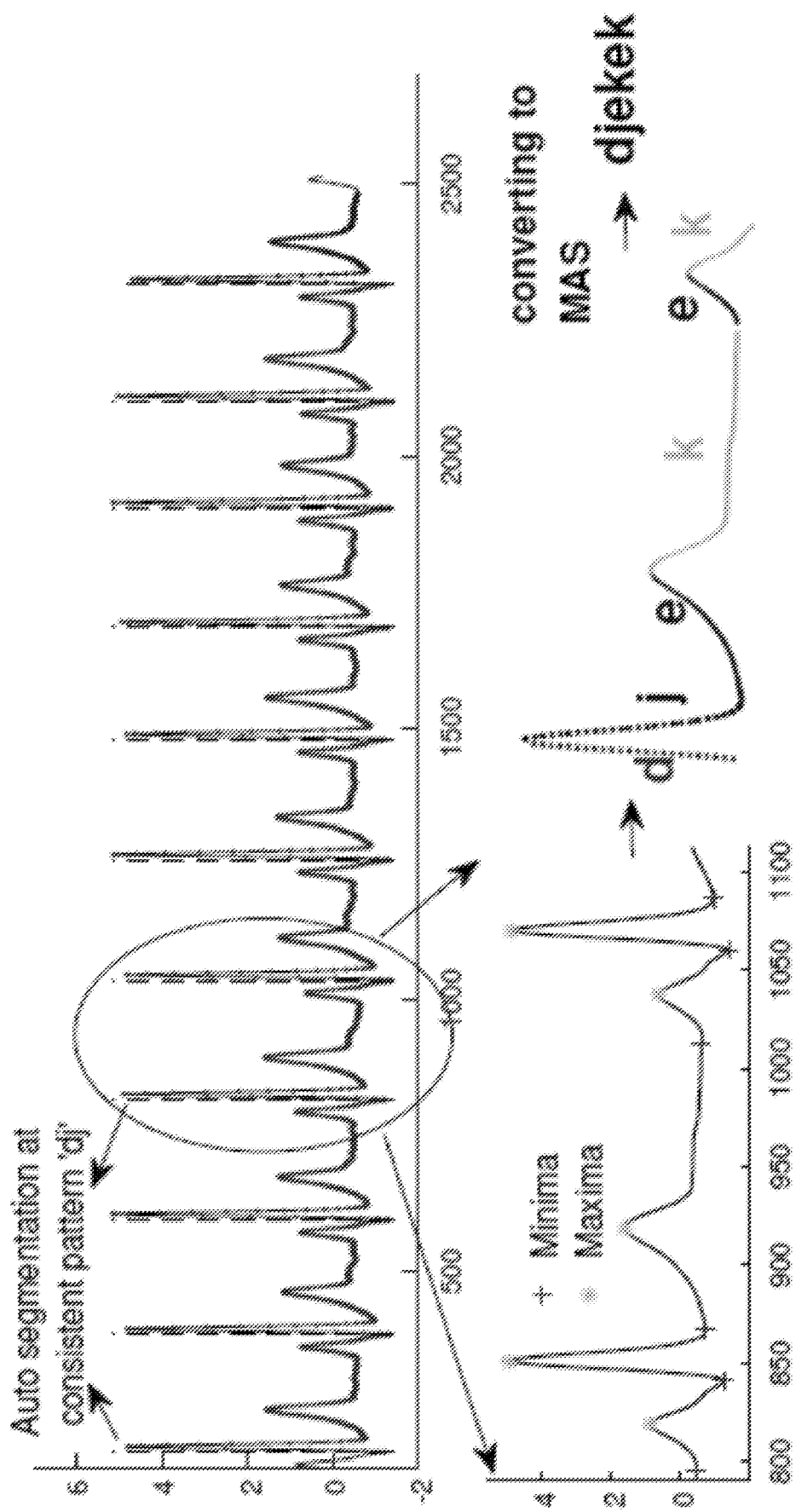
FIG. 2 shows an example of the ECG signal along with the symbolic representation of the signal according to an embodiment of the disclosure.

Referring now to the drawings, and more particularly to FIG. 1 through FIG. 3, where similar reference characters denote corresponding features consistently throughout the figures, there are shown preferred embodiments and these embodiments are described in the context of the following exemplary system and/or method.

According to an embodiment of the disclosure, a system 100 for detecting anomaly and discovering pattern in a signal using symbolic representation of the signal is shown in FIG. 1. The signal is a physiological signal captured from a person. The disclosure uses a unique technique for symbolic representation of the signal. The symbolic representation of the signal is then used to retain the relevant information from the signal. The disclosure is using features that are mainly dependent on the morphology and strictly rising/increasing and falling/decreasing edges of the signal by exploiting the nature of rise and fall of the signal. Additionally the system possesses more generalization capability than the existing scheme in terms of granularity. The system 100 discriminate between a normal signal and an anomalous signal with consistency.

According to an embodiment of the disclosure, the system 100 further comprises a sensor 102, a derivation module 104, a memory 106 and a processor 108 as shown in the block diagram of FIG. 1. The processor 108 works in communication with the memory 106. The processor 108 further comprises a plurality of modules. The plurality of modules accesses the set of algorithms stored in the memory 106 to perform a specific task. The processor 108 further comprises a maxima and minima finding module 110, a feature derivation module 112, a clustering module 114, a symbolic representation module 116 for the signal, and anomaly identification module 118.

The sensor 102 is a physiological sensor configured to capture the physiological signal from the signal. The system 100 further comprises a preprocessor 120 for preprocessing the sensed signal. In an example of the present disclosure, an ECG signal is captured using any available ECG sensor. An exemplary ECG waveform along with their symbolic representation is shown in FIG. 2. The figures show the sample ECG waveform is converted in to "djekek" morphological symbolic awareness form. Though it should be appreciated that the use of the system 100 for detecting anomaly in any other physiological signal is well within the scope of this disclosure. The sensed signal is time series signal with a plurality of time points in the signal. The time series is a sequence of data points sampled at equal time intervals obtained over a certain period of time. Let $T_s$ be a time series having 'n' data points sampled at discrete time instants 1, 2, 3, ... , n. Then $T_s$ is represented as:

$Ts=\{a_1, a_2, a_3, \ldots, a_k, \ldots, a_{n-1}, a_n\}$, $a_k \in \mathbb{R}$ $\forall$ k, where $a_k$ is the amplitude of signal at various time points.

According to an embodiment of the disclosure the derivation module 104 is configured to provide a dissimilarity metric as explained in the later part of the disclosure.

According to an embodiment of the disclosure, the system 100 comprises the maxima and minima finding module 110. The maxima and minima finding module 110 is configured to finding a plurality of maxima points and a plurality of minima points in the signal. The plurality of maxima points and the plurality of minima points are following morphology of the signal. The plurality of maxima points and the plurality of minima points are exploiting strictly rising and falling edges of the signal. The plurality of maxima points comprises of a local maxima. The local maxima, $a_{max}$ is said to occur in the time series Ts at the location 'max' with amplitude $a_{max}$ if amax−2<amax−1<amax>amax+1>amax+2. Similarly, the plurality of minima points comprises a local minima. The local minima, $a_{min}$ is said to occur in the time series $T_s$ at the location 'min' with amplitude amin if amin−2>amin−1>amin<amin+1<amin+2. In the respect to this, plurality of maxima and minima points will be $\{a_{max}^i\}_{i=1}^{N_{max}}$, $\{a_{min}^j\}_{j=1}^{N_{min}}$.

It should be appreciated that in between two local maxima there exists a local minima, and there exists a local maxima in between two local minima. Thus, if there are k local maxima and k local minima occurring at locations $max_1$, $max_2 \ldots$ , $max_k$ and $min_1$, $min_2 \ldots$ , $min_k$ respectively and if we write these locations of local maxima and minima in increasing order, starting with, say, a local maxima, then this sequence is represented as $max_1 < min_1 < max_2 < min_2 \ldots < max_k < min_k$. These maxi's and mini's are known as extrema points.

According to an embodiment of the disclosure, the system 100 further comprises the feature derivation module 112. The feature derivation module 112 is configured to derive a plurality of features using the plurality of maxima points and the plurality of minima points which are adjacent to each other. There are four types if plurality of features. The plurality of features comprises (i) amplitude difference between minima to maxima points which are adjacent to each other, (ii) number of sampling points between minima to maxima points which are adjacent to each other, (iii) amplitude difference between maxima to minima points which are adjacent to each other and (iv) number of sampling points between maxima to minima points which are adjacent to each other. The plurality of features are mainly dependent on the morphology and strictly rising/increasing and falling/decreasing edges of the signal. The amplitude difference (A) is defined as the difference between the amplitudes of two consecutive extrema points. For this example, minima to maxima amplitude difference ($A_{mM}$) and maxima to minima amplitude difference ($A_{Mm}$) will be $$A_{mM} = \{A_{mM}^k = |a_{max}^{k+1} - a_{min}^k|\}$$

$$A_{Mm} = \{A_{Mm}^k = |a_{min}^k - a_{max}^k|\}$$

$\forall k=1,2,3, \ldots \min(N_{max}, N_{min})$ $A_{mM}^k$ is the $k^{th}$ element of the $A_{mM}$ (i.e. $k^{th}$ min to MAX "slice") that corresponds to a portion/slice in the original time series occurring through indices/locations $a_{min}^k$ to $a_{max}^{k+1}$. This min-to-MAX slice is represented as one amplitude value/observation.

According to an embodiment of the disclosure, the system 100 further comprises the clustering module 114. The clustering module 114 is configured to perform a proximity based clustering on the plurality of features to get a cluster centroid values corresponding to each of the plurality of features. Thus, it will give $\{I_{mM}, C_{mM}\}$ and $\{I_{mM}, C_{Mm}\}$ having $E_{mM}$ and $E_{Mm}$ number of cluster respectively.

Here, I contains the cluster indices of each observation of data ($A_{mM}^k$) and C denotes the cluster centroid of the partitioned data Initially a value is set for maximum number of clusters formed for the plurality of derived features. Further, at least one of the step is performed based on the distribution of the plurality of features. If the plurality of features has Gaussian distribution, then dividing the plurality of features into K equi-probable regions of Gaussian distribution and finding the cluster centroids of the derived features. Else, arranging the plurality of features in the ascending order and finding the first difference of data stored in dataset of derived features; breaking the first difference of data stored in dataset of derived features into two clusters where maximum difference occurs; and checking a condition for the number of cluster.

According to an embodiment of the disclosure, the system 100 further comprises the symbolic representation module 116 for the signal. The symbolic representation module 116 is configured to represent the cluster centroid values in the form of a plurality of symbols in the descending order of the cluster centroid values in terms of the amplitude difference and the number of sampling points corresponding to minima to maxima points and maxima to minima points. The symbolic representation module 116 further configured to represent the signal into a symbolic form using the plurality of symbols.

The disclosure provides discovery of a pattern atom using symbols. The symbolic representation retains most of the information in terms of a smaller value of squared error. Further, the step of representing the string of symbols using minima to maxima points and maxima to minima points encoded by their corresponding occurrences of cluster centroid values in their consecutive order of occurrences. The encoding of occurrence of consecutive minima to maxima points and consecutive maxima to minima points is based on a pair of symbols known as the pattern atom. The string of symbols further comprising pattern atom with highest regularity in their occurrences. The representation of the signal further comprise segmenting the string of symbols using consistent pattern atom. Similarly, the representation of the signal further comprises merging of string of symbols with a corresponding plurality of segments.

The pattern is the symbolically represented entity that represents the increase-decrease morphology. For example, 'xy' is a pattern with symbols/pattern atoms x ∈ {'d', 'e', 'f'} and y ∈ {'j', 'k', 'l'}. Here, {'d', 'e', 'f'} represent the symbols used to encode the clusters over all the amplitude differences of increasing portions in the time series in the descending order of the centroid values. Similarly, {'j', 'k', 'l'} represent the symbols for decreasing portions. In this way, 'dj' represents all those portions in the time series that have high increase and high decrease with high amplitude differences. Similarly, 'ek' represents increase-decrease portions with medium amplitude differences. However, 'fl' represents small increase-decrease portions occurring due to perturbations or relatively low amplitude differences in the time series. xy={'dj', 'dk', 'dl', 'ej', 'ek', 'el', 'fj', 'fk', 'fl'} also termed as pattern atom are used to encode the signal symbolically.

For each pattern atom in xy, sequence of differences between consecutive occurrences of the same pattern atom are evaluated from the complete symbolically encoded signal. Let us represent this sequence of differences by $S_d$. Let $i_{xy}$=1, 2, 3, . . . , k be unique integers occurring in $S_d$ and $f_i^{xy}$=$f_1$, $f_2$, . . . , $f_k$ be the number of occurrences of these unique $i_{xy}$ in $S_d$. Then, $$\mu_{xy} = \frac{\Sigma(i_{xy} \times f_i^{xy})}{\Sigma(f_i^{xy})}, \sigma_{xy} = \sqrt{\frac{\Sigma f_i^{xy}(i_{xy} - \mu_{xy})^2}{\Sigma(f_i^{xy})}}$$

An increase-decrease morphology $y_{cp}$, $x \in \{\text{'d'}, \text{'e'}, \text{'f'}\}$, $y \in \{\text{'j'}, \text{'k'}, \text{'l'}\}$ is said to be consistent pattern $xy_{cp}$={xy, s.t $\sigma_{xy_{cp}} < \sigma_{xy_k} \forall k$=1, 2, . . . , |xy|, k≠cp}

According to an embodiment of the disclosure, the derivation module 104 is configured to provide the dissimilarity metric as the input to the system 100. The dissimilarity metric is a function of regularity of the string of symbols and a distance measured between the strings of symbols for detecting anomalous patterns. The dissimilarity metric between two symbolic strings (sequences) S1 and S2 is defined as follows:

Let, $S_1 \approx (S_{11}, S_{12}, \ldots, S_{1\beta})$ and $S_2 \approx (S_{21}, S_{22}, \ldots, S_{2\alpha})$, where $\beta > \alpha$. $(S_{11}, S_{12}, \ldots, S_{1\beta})$ and $(S_{21}, S_{22}, \ldots, S_{2\alpha})$ are consecutively occurring symbols. CC(S) denotes the cluster centroids of the symbols. For example, CC(d) denotes the cluster centroid of the largest amplitude difference of the corresponding increasing edge of the time series. Similarly, CC(e) denotes the cluster centroid of medium amplitude differences, and CC(f) denotes the cluster centroid of the smallest amplitude differences. Similarly, CC(j), CC(k), CC(l) are the cluster centroids in the descending order of their amplitude differences for decreasing edge of the time-series.

$$d(S_1, S_2) = \sqrt{\sum_{\delta=0,2,4,\ldots,(\beta-\alpha)} \sum_{r=1}^{\delta} |CC(S_{1(\delta+r)}) - CC(S_{2r})|^2}$$

According to an embodiment of the disclosure, the system 100 further comprises the anomaly detection module 118. The anomaly finding module 118 is configured to find the anomalous pattern in the signal using the dissimilarity metric.

Figure 3A:
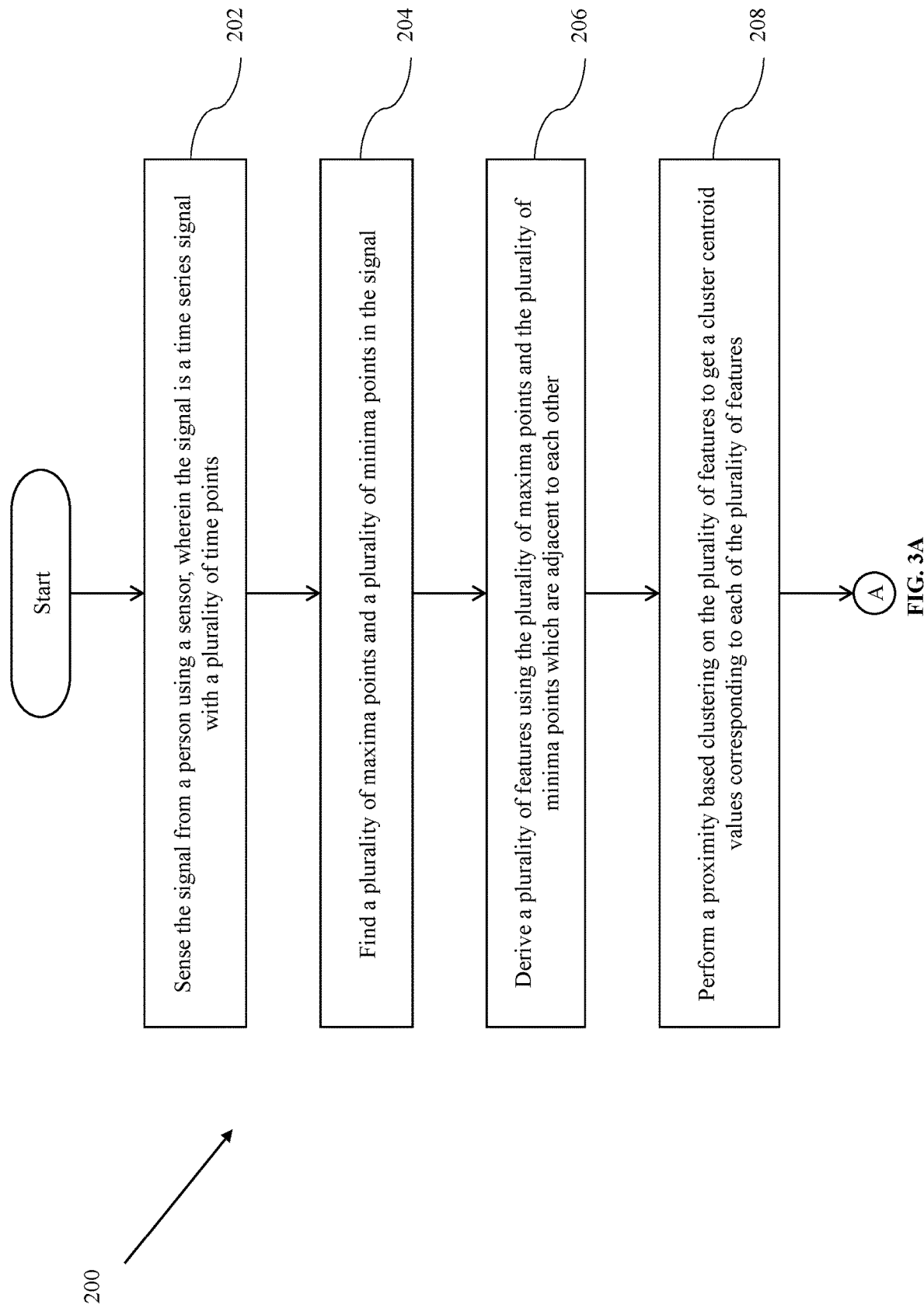

According to an embodiment of the disclosure, the system 100 further comprises measurement of the regularity in the interval of the frequency of occurrences of the pattern atoms In operation, a flowchart 200 illustrating the steps of detecting anomaly and discovering pattern in a signal using symbolic representation of the signal is shown in FIG. 3A-3B. Normally, the signal is a physiological signal and ECG signal have been used in an example of the present disclosure. Initially, at step 202, sensing the signal from a person using a sensor, wherein the signal is a time series signal with a plurality of time points. In the next step 204, a plurality of maxima points and a plurality of minima points are detected in the signal. The plurality of maxima points and the plurality of minima points are strictly following the rising edge and falling edge of the signal.

In the next step 206, the plurality of features are derived using the plurality of maxima points and the plurality of minima points which are adjacent to each other, wherein the plurality of features comprises amplitude difference and number of sampling points between minima to maxima points which are adjacent to each other and amplitude difference and number of sampling points between maxima to minima points which are adjacent to each other. Further at step 208, a proximity based clustering is performed on the plurality of features to get a cluster centroid values corresponding to each of the plurality of features.

In the next step 210, the cluster centroid values are represented in the form of a plurality of symbols in the descending order of the cluster centroid values in terms of the amplitude difference and the number of sampling points corresponding to minima to maxima points and maxima to minima points. At step 212, the signal is then represented into the symbolic form using the plurality of symbols, wherein the symbolic form comprising one or more string of symbols. The symbols are generated using the features mainly dependent on the morphology and strictly rising and falling edges of the signal. The symbolic representation retains most of the information in terms of a smaller value of squared error.

In the next step 214, the dissimilarity metric is provided. The dissimilarity metric is a function of: regularity of the string of symbols, and a distance measure between the strings of symbols for detecting anomalous patterns. And finally at step 216, and the anomalous pattern are detected in the signal using the dissimilarity metric.

According to an embodiment of the disclosure, the system 100 can also be explained with the help of the example of following three algorithms. The first algorithm provides the symbolic encoding of the input time series signal. The second algorithm performs the proximity based clustering. The third algorithm is used to detect discord or anomalous pattern using morphological aware symbolic (MAS) representation.

---

Algorithm1: MAS

---

Input: Raw Time Series sensor signal Ts of length n as per Definition 1.
Output: Symbolic encoding of Ts as S.
1: Find all maxima $a_{max_i}$; i = 1, 2; 3, ..., $N_{max}$ and minima $a_{min_i}$, i = 1, 2, 3, ..., $N_{min}$ Indices in the time series Ts.
Note that | $N_{min}$ − $N_{max}$ | ≤ 1.
2: Find consecutive Max-min/min-Max pairs.
3: Find $Amp_{MaxMin}^k$ and $Amp_{MinMax}^k$ $\forall$ k = 1, 2, 3, ..., min($N_{min}$, $N_{max}$)
4: Indices$_{MaxMin}$, ClusterCentroids$_{MaxMin}$ = Call_Clustering ($Amp_{MaxMin}^k$)
5: Indices$_{MinMax}$, ClusterCentroids$_{MinMax}$ = Call_Clustering ($Amp_{MinMax}^k$)
6: Encode Cluster centroids MinMax into symbolic strings
    S1 and map back to corresponding indices of cluster.
7: Encode Cluster centroids MaxMin into symbolic strings
    S2 and map back to corresponding indices of cluster.
8: S = S1 ∪ S2
9: Do sorting S as per the time series index.
10: return EncodedString S
11: function Call_Clustering(Amp)
12:   return Cluster centroids
13: end function

---

Algorithm 2 - Proximity based data balanced clustering:
Call Clustering ( )

---

Input: Data set X maximum number of Cluster K
Output: ClusterCentroid Ck.
1: if (isGaussian(X))
2:    Divide the data into K equi-probable
    Regions of Gaussian distribution
3: return ClusterCentroid $C_k$
4: else
5:    Call ClusterDivide(X)

-continued

Algorithm 2 - Proximity based data balanced clustering:
Call Clustering ( )

```
 6:     if (NumberofCluster = K)
 7:         return ClusterCentroid C_k
 8:     else Call SignificantCluster(C_k, τ)
 9:         if (1)
10:             return Indices to be merged with bigger clusters
11:         else
12:             if (isGaussian(C_k))
13:                 return ClusterCentroid C_k
14:             else
15:                 return Go to Step 5
16:             end
17:         end
18:     end
19: end
20: function Call_ClusterDivide(v)
21:     Arrange v in ascending order
22:     v_d = Take first difference of v
23:     Break v_D in two clusters where max difference occurs
24:     return Clusters
25: end function
26: function Call_SignificantCluster(v, τ)
27:     insignificance_thresh = ceil(τ * length(v)/100)
28:     if (length(v) ≥ insignificance_thresh)
29:         return 1
30:     else
31:         return 0
32:     end
33: end function
```

Algorithm 3 - Discord/Anomalous pattern discovery using MAS

Input: Symbolic Encoding S of Time series Ts
Output: K Discords
1: Find repeating pattern Rp using Call_ConsistentPattern(S).
2: Segment S using consistent pattern $R_p^i$ to $R_{p+1}^i$ ∀ i = 1, 2, 3, ... |$R_p$|
    to form pattern strings Ps s.t $P_s^i$ starts with $R_p$.
3: Remove from each $P_s^i$ the symbols corresponding to smallest perturbations.
4: for iter = 1 to |$P_s$| do
5:     str1 = Ps(iter)
6:     for jter = 1 to |$P_s$| do
7:         str2 = Ps(jter)
8:         DD(iter,jter) = freqstr2 * Call DisimilarityMeasure(str1,str2)
9:     end for
10:    Ds(iter) = sum(DD(iter;:))/sum(freq)
11: end for
12: $P_s^{ordered}$ = Order $P_s$ using sort($D_s$, 'descend')
13: return Top-K discords are the corresponding indices of
    Top K elements $P_s^{ordered}$
14: function Call_ConsistentPattern(S) Find the consistent pattern in
patterns using Definition 6.
15: end function
16: function Call_DissimilarityMeasure(str1,str2)
17:    Find the dissimilarity measure between strings (subsequence)
according to definition 7.
18:    return dist
19: end function The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provides a method and system for detecting anomaly in the signal using a morphological aware symbolic representation of the signal. The method thus treat the problem of relevant information loss during the symbolic representation of the signal.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for detecting anomaly and discovering pattern in a signal using symbolic representation of the signal, the method comprising a processor implemented steps of:
    sensing the signal from a person using a sensor, wherein the signal is a time series signal with a plurality of time points (202);
    finding a plurality of maxima points and a plurality of minima points in the signal, wherein the plurality of maxima points and the plurality of minima points are following morphology of the signal (204);
    deriving a plurality of features using the plurality of maxima points and the plurality of minima points which are adjacent to each other, wherein the plurality of features comprises amplitude difference and number of sampling points between minima to maxima points which are adjacent to each other and amplitude difference and number of sampling points between maxima to minima points which are adjacent to each other (206);
    performing a proximity based clustering on the plurality of features to get cluster centroid values corresponding to each of the plurality of features (208);
    representing the cluster centroid values in a form of a plurality of symbols in descending order in terms of the amplitude difference and the number of sampling points corresponding to minima to maxima points and maxima to minima points (210);
    representing the signal into the symbolic form using the plurality of symbols, wherein the symbolic form comprising one or more strings of symbols (212);
    deriving a dissimilarity metric, wherein the dissimilarity metric is a function of: regularity of the strings of symbols, and
    a distance measure between the string of symbols for detecting anomalous patterns (214); and
    detecting the anomalous pattern in the signal using the dissimilarity metric (216).

2. The method of claim 1, further comprising: representing the string of symbols using minima to maxima points and maxima to minima points encoded by their corresponding occurrences of cluster centroid values in their consecutive order of occurrences.

3. The method of claim 2, wherein the encoding of occurrence of consecutive minima to maxima points and consecutive maxima to minima points are based on a pair of symbols known as pattern atoms.

4. The method of claim 3, wherein the string of symbols further comprising pattern atom with highest regularity in their occurrences.

5. The method of claim 4, further comprising measuring regularity in the interval of the frequency of occurrences of the pattern atoms.

6. The method of claim 1, wherein the step of representing the signal further comprising segmenting the string of symbols using consistent pattern atom.

7. The method of claim 1, wherein the step of representing the signal further comprising merging of string of symbols with a corresponding plurality of segments.

8. The method of claim 1, wherein the plurality of features further comprising number of points from adjacent minima to maxima and a number of points from adjacent maxima to minima.

9. The method of claim 1, wherein the plurality of maxima points and the plurality of minima points are exploiting strictly rising and falling edges of the signal.

10. The method of claim 1, further comprising the step of preprocessing the sensed signal, wherein the sensed signal is a physiological signal captured from a physiological sensor.

11. The method of claim 1, wherein the step of performing the proximity based clustering further comprising:
    receiving the plurality of features derived from the signal;
    setting a value for maximum number of clusters formed for the plurality of derived features;
    performing at least one step based on the distribution of plurality of features:
    if the plurality of features has Gaussian distribution, then
        dividing the plurality of features into K equi-probable regions of Gaussian distribution and finding the cluster centroids of the derived features,
    else,
        arranging the plurality of features in the ascending order and finding the first difference of data stored in dataset of derived features;
        breaking the first difference of data stored in dataset of derived features into two clusters where maximum difference occurs; and
        checking a condition for the number of cluster.

12. A system for detecting anomaly and pattern discovery in a signal using symbolic representation of the signal, the system comprising:
    a sensor (102) for sensing the signal from a person, wherein the signal is a time series signal with a plurality of time points;
    a memory (106); and
    a processor (108) in communication with the memory (106), the processor (108) is configured to:
        find a plurality of maxima points and a plurality of minima points in the signal, wherein the plurality of maxima points and the plurality of minima points are following morphology of the signal;
        derive a plurality of features using the plurality of maxima points and the plurality of minima points which are adjacent to each other, wherein the plurality of features comprises an amplitude difference and a number of sampling points between minima to maxima points which are adjacent to each other and the amplitude difference and a number of sampling points between maxima to minima points which are adjacent to each other;

perform a proximity based clustering on the plurality of features to get a cluster centroid values corresponding to each of the plurality of features;

represent the cluster centroid values in a form of a plurality of symbols in descending order in terms of the amplitude difference and the number of sampling points corresponding to minima to maxima points and maxima to minima points, and represent the signal into the symbolic form using the plurality of symbols, wherein the symbolic form comprising one or more string of symbols;

derive a dissimilarity metric, wherein the dissimilarity metric is a function of regularity of the strings of symbols, and a distance measured between the string of symbols for detecting anomalous patterns; and detect the anomalous pattern in the signal using the dissimilarity metric.

13. A computer program product comprising a non-transitory computer readable medium having a computer readable program embodied therein, wherein the computer readable program, when executed on a computing device, causes the computing device to:

sense the signal from a person using a sensor, wherein the signal is a time series signal with a plurality of time points (202);

find a plurality of maxima points and a plurality of minima points in the signal, wherein the plurality of maxima points and the plurality of minima points are following morphology of the signal (204);

derive a plurality of features using the plurality of maxima points and the plurality of minima points which are adjacent to each other, wherein the plurality of features comprises amplitude difference and number of sampling points between minima to maxima points which are adjacent to each other and amplitude difference and number of sampling points between maxima to minima points which are adjacent to each other (206);

perform a proximity based clustering on the plurality of features to get cluster centroid values corresponding to each of the plurality of features (208);

represent the cluster centroid values in a form of a plurality of symbols in descending order in terms of the amplitude difference and the number of sampling points corresponding to minima to maxima points and maxima to minima points (210);

represent the signal into the symbolic form using the plurality of symbols, wherein the symbolic form comprising one or more strings of symbols (212);

derive a dissimilarity metric, wherein the dissimilarity metric is a function of:
 regularity of the strings of symbols, and
 a distance measure between the string of symbols for detecting anomalous patterns (214); and detect the anomalous pattern in the signal using the dissimilarity metric (216).

14. The computer program product of claim 13, causing the computing device to represent the string of symbols using minima to maxima points and maxima to minima points encoded by their corresponding occurrences of cluster centroid values in their consecutive order of occurrences.

15. The computer program product of claim 14, wherein the encoding of occurrence of consecutive minima to maxima points and consecutive maxima to minima points are based on a pair of symbols known as pattern atoms.

16. The computer program product of claim 15, wherein the string of symbols further comprising pattern atom with highest regularity in their occurrences.

17. The computer program product of claim 15, causing the computing device to measure regularity in the interval of the frequency of occurrences of the pattern atoms.

18. The computer program product of claim 15, causing the computing device to segment the string of symbols using consistent pattern atom.

19. The computer program product of claim 13, causing the computing device to merge string of symbols with a corresponding plurality of segments.

20. The computer program product of claim 13, wherein the plurality of features further comprises number of points from adjacent minima to maxima and a number of points from adjacent maxima to minima.

* * * * *